United States Patent [19]

Fischell et al.

[11] Patent Number: 5,100,425
[45] Date of Patent: Mar. 31, 1992

[54] EXPANDABLE TRANSLUMINAL ATHERECTOMY CATHETER SYSTEM AND METHOD FOR THE TREATMENT OF ARTERIAL STENOSES

[75] Inventors: Robert F. Fischell, Dayton, Md.; Tim A. Fischell, Los Altos, Calif.

[73] Assignee: MedInTec R&D Limited Partnership, Dayton, Md.

[21] Appl. No.: 407,192

[22] Filed: Sep. 14, 1989

[51] Int. Cl.⁵ .................................................. A61B 17/22
[52] U.S. Cl. .................................................. 606/159; 604/22
[58] Field of Search ............................ 604/22, 96–103; 128/751–755; 606/159, 191, 194, 168, 170

[56] References Cited

U.S. PATENT DOCUMENTS

| | | | |
|---|---|---|---|
| 2,816,552 | 12/1957 | Hoffman | 606/159 |
| 3,670,732 | 6/1972 | Robinson | 606/160 |
| 4,200,111 | 4/1980 | Harris | 128/751 |
| 4,631,052 | 12/1986 | Kensey | 606/159 |
| 4,653,496 | 3/1987 | Bundy et al. | 606/159 |
| 4,696,667 | 9/1987 | Masch | 604/22 |
| 4,768,508 | 9/1988 | Chin et al. | 604/22 |
| 4,784,636 | 11/1988 | Rydell | 606/159 |
| 4,842,579 | 6/1989 | Shiber | 606/159 |
| 4,857,045 | 8/1989 | Rydell | 606/159 |
| 4,895,560 | 1/1990 | Papantonakos | 604/22 |
| 4,917,085 | 4/1990 | Smith | 606/159 |
| 4,921,484 | 5/1990 | Hillstead | 606/159 |
| 4,926,858 | 5/1990 | Gifford, III et al. | 606/170 |
| 4,966,604 | 10/1990 | Reiss | 606/159 |

Primary Examiner—C. Fred Rosenbaum
Assistant Examiner—William W. Lewis

[57] ABSTRACT

An expandable transluminal atherectomy catheter system (10) is provided which includes an expandable transluminal atherectomy catheter (ETAC) (20), a balloon-on-a-guide wire (30), a sheathing catheter (40) and a rotator unit (60). The balloon-on-a-guide wire (30) is advanced through an arterial system to a predetermined point. The ETAC (20) within a sheathing catheter (40) is advanced over the guide wire cylinder (32). Prior to injection of a medium the sheathing catheter (40) is pulled back to allow spokes (24) of ETAC (20) to expand. The system (10) removes atheromatous plaque to a larger diameter than the diameter of the catheter (20) where it percutaneously penetrates the skin by the anterograde transluminal catheter whose distal end can be expanded after insertion of the catheter (20) into an artery.

7 Claims, 3 Drawing Sheets

EXPANDABLE TRANSLUMINAL ATHERECTOMY CATHETER SYSTEM AND METHOD FOR THE TREATMENT OF ARTERIAL STENOSES

BACKGROUND OF THE INVENTION

1. Field of the Invention

This invention constitutes a means and method for the treatment of arterial stenoses by the use of an Expandable Transluminal Atherectomy Catheter (ETAC) system.

2. Description of the Prior Art

Arterial stenoses are becoming increasingly common as life expectancy increases. There are numerous treatments to open stenotic lesions including surgical interventions such as endarterectomy and by-pass surgery using veins or artificial graft materials. Ballon angioplasty is becoming increasingly popular for the dilation of arterial stenoses. More recently atherectomy, the excision from the body of atheromatous plaque, has been successfully used to open arterial stenoses. U.S. patent application Ser. No. 874140 filed by R. E. Fischell and T. A. Fischell on June 13, 1986 entitled "A Guide Wire Following Tunneling Catheter System for Transluminal Arterial Atherectomy" first described a forward motion (anterograde) cutting, single lumen atherectomy catheter that is advanced over a guide wire. A disadvantage of that and other anterograde cutting atherectomy devices is that they can only cut a hole in the stenosis as large as their own fixed diameter. This is a distinct disadvantage in that it is generally preferable to percutaneously enter the femoral artery at the groin with a catheter no larger than 3.0 mm in diameter, and then to excise plaque close to the arterial wall for arteries that are larger in diameter than 3.0 mm. For example it would be desirable to remove plaque to the diameter of the unoccluded arterial lumen for a 4 mm diameter coronary artery, a 5 mm diameter femoral or renal artery and a 5 to 7 mm diameter internal or common carotid artery. Although U.S. Pat. No. 4,765,332, issued Aug. 23, 1988 to R. E. Fischell and T. A. Fischell entitled "Pullback Atherectomy Catheter System" describes an effective retrograde atherectomy catheter system, it also does not teach a method for entering the artery with a 3 mm diameter catheter and removing plaque to larger diameters. U.S. patent application Ser. No. 153,912 filed Feb. 9, 1988 by R. E. Fischell and T. A. fischell entitled "Expandable Pullback Atherectomy Catheter" did however show a method for excising plaque by a cutting means that could expand at its distal end to a larger diameter than the basic diameter of the catheter body after insertion into the artery. However, the retrograde cutting device must first pass through the stenosis before expanding which could be disadvantage, particularly for treating a severely narrowed artery.

U.S. Pat. No. 4,631,052 by K. R. Kensey entitled "Method and Apparatus for Surgically Removing Remote Deposits" describes a means for distally occluding the artery just beyond the stenosis to prevent the distal arterial embolization of particulate debris that might be released during the atherectomy procedure. However, Kensey's invention does not teach the unique occlusive balloon inflation means suggested herein which uses a hollow guide wire to provide fluid communication between the balloon and a source of fluid that lies outside the body.

SUMMARY OF THE INVENTION

The Expandable Transluminal Atherectomy Catheter (ETAC) system described herein overcomes much of the shortcomings of prior art atherectomy devices. The catheter has a distally located expandable cutting means which expands when a sheathing catheter is pulled back in a proximal direction. The outside diameter of the sheathing catheter would typically be 3 mm (9 French) while the tip could expand to as large as 10 mm diameter (30 French). The entire system would be percutaneously inserted at the groin into the femoral artery and advanced over a previously inserted hollow guide wire that had passed through the stenosis. The distal tip of the guide wire would include a balloon that would be inflated after the balloon was placed distal to the stenosis in order to temporarily occlude the artery just prior to advancing the ETAC. As soon as the balloon is inflated to occlude the artery, a side hole in the hollow guide wire just proximal to the balloon would serve as the point from which a contrast flush solution, injected at the guide wire's proximal end outside the patient's body, would enter the artery. Simultaneously with the initiation of the flush solution, the expandable distal tip of the ETAC would be advanced through the stenosis while rotating and also applying a suction at the catheter's distal end which is in fluid communication with the proximal end of the ETAC located outside the patient's body. As soon as the distal tip is advanced through the entire length of the stenosis, the rotation of the ETAC is stopped, and, 0 to 60 seconds later, the suction and the infusion of flushing solution would also be stopped. The occlusive balloon is then deflated and the entire ETAC system is removed from the artery.

Thus, one object of this invention is to provide a means for removing atheromatous plaque to a larger diameter than the diameter of the catheter where it percutaneously penetrates the skin by means of an anterograde transluminal catheter whose distal end can be expanded after insertion of the catheter into the artery.

Another object of this invention is to prevent the release of distal emboli into the blood stream by deploying an inflatable, occluding balloon distal to the stenosis so as to occlude the artery during and for a short time after the atherectomy procedure.

Still another object of this invention is to flush out the cut plaque using a source of flushing liquid injected distal to the stenosis that is removed by a suction source applied at the proximal end of the ETAC which suction is in fluid communication with the distal, cutting end of the ETAC.

Still another object of this invention is to use the same fluid that flows through a hollow guide wire to both inflate an occlusive balloon and flush atheromatized plaque back through the catheter to a suction source attached at the catheter's proximal end that is located outside of the patient.

Still another object of this invention is to provide an expandable grinding means for an atherectomy catheter.

Still another object of this invention is to provide the combination of both grinding means and cutting means in a single atherectomy device.

DETAILED DESCRIPTION OF THE INVENTION

Figure 1:
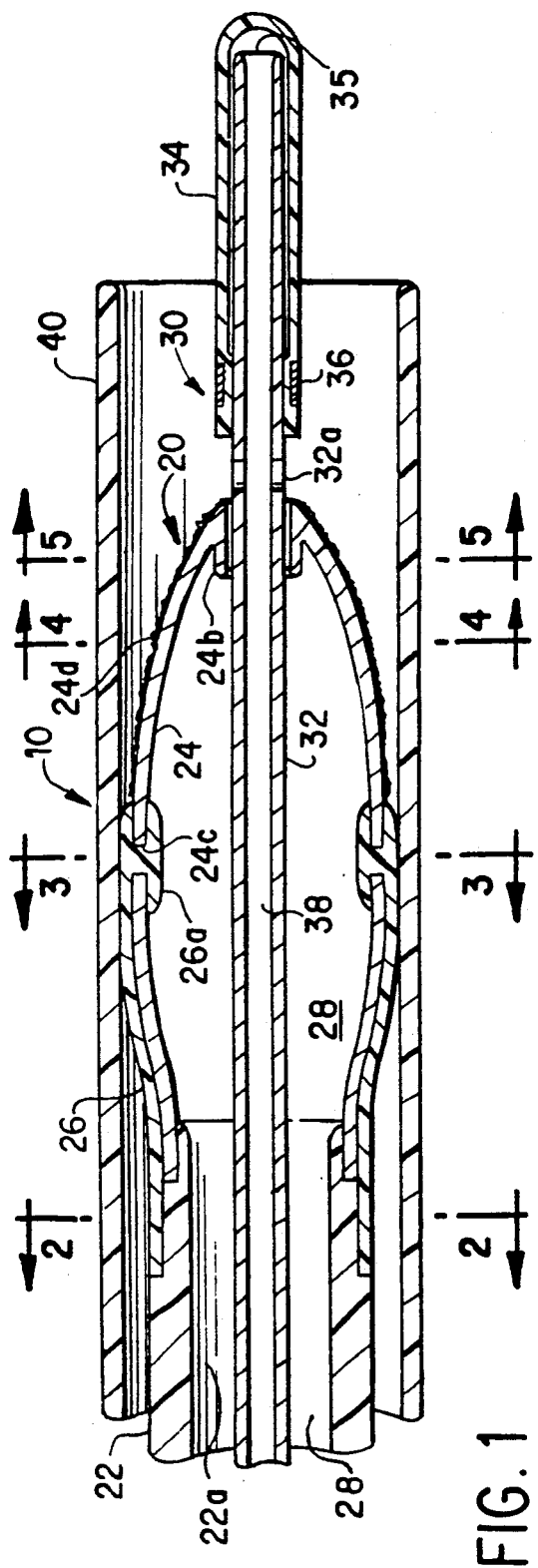
FIG. 1 is a longitudinal cross-sectional view of the distal portion of the Expandable Transluminal Atherectomy Catheter (ETAC) system in its contracted state.
Figure 3:
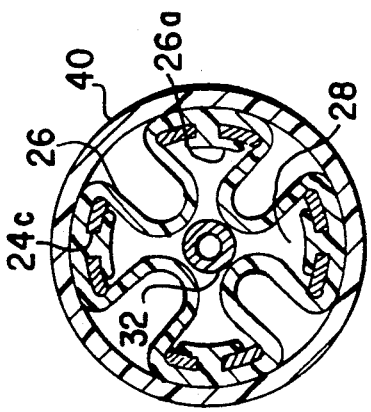
FIG. 3 is a transverse cross-sectional view of the ETAC system at a point along its length that will expand to its maximum diameter; specifically at 3—3 of FIG. 1.
Figure 2:
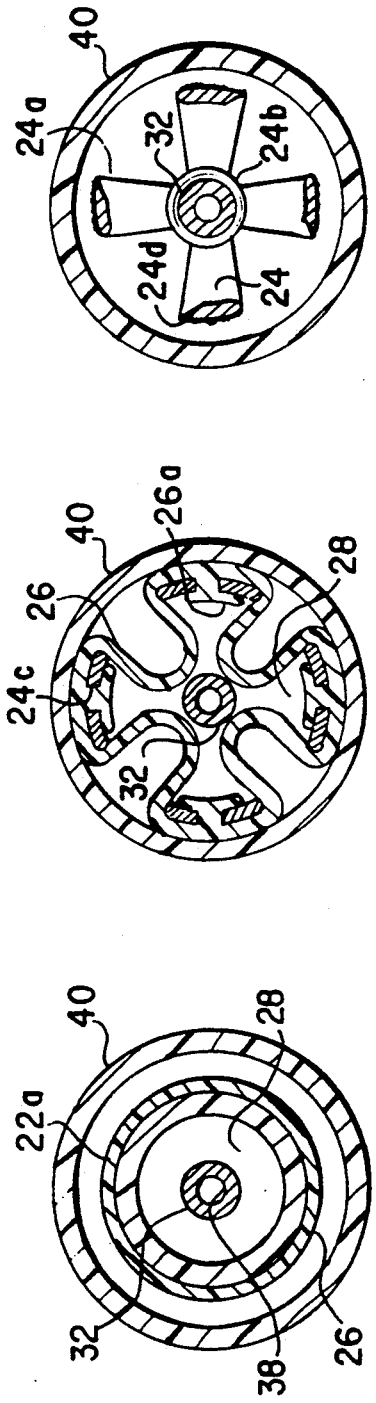
FIG. 2 is a transverse cross-sectional view of the ETAC system at the distal end of the torquing catheter; specifically at 2—2 of FIG. 1.
Figure 8:
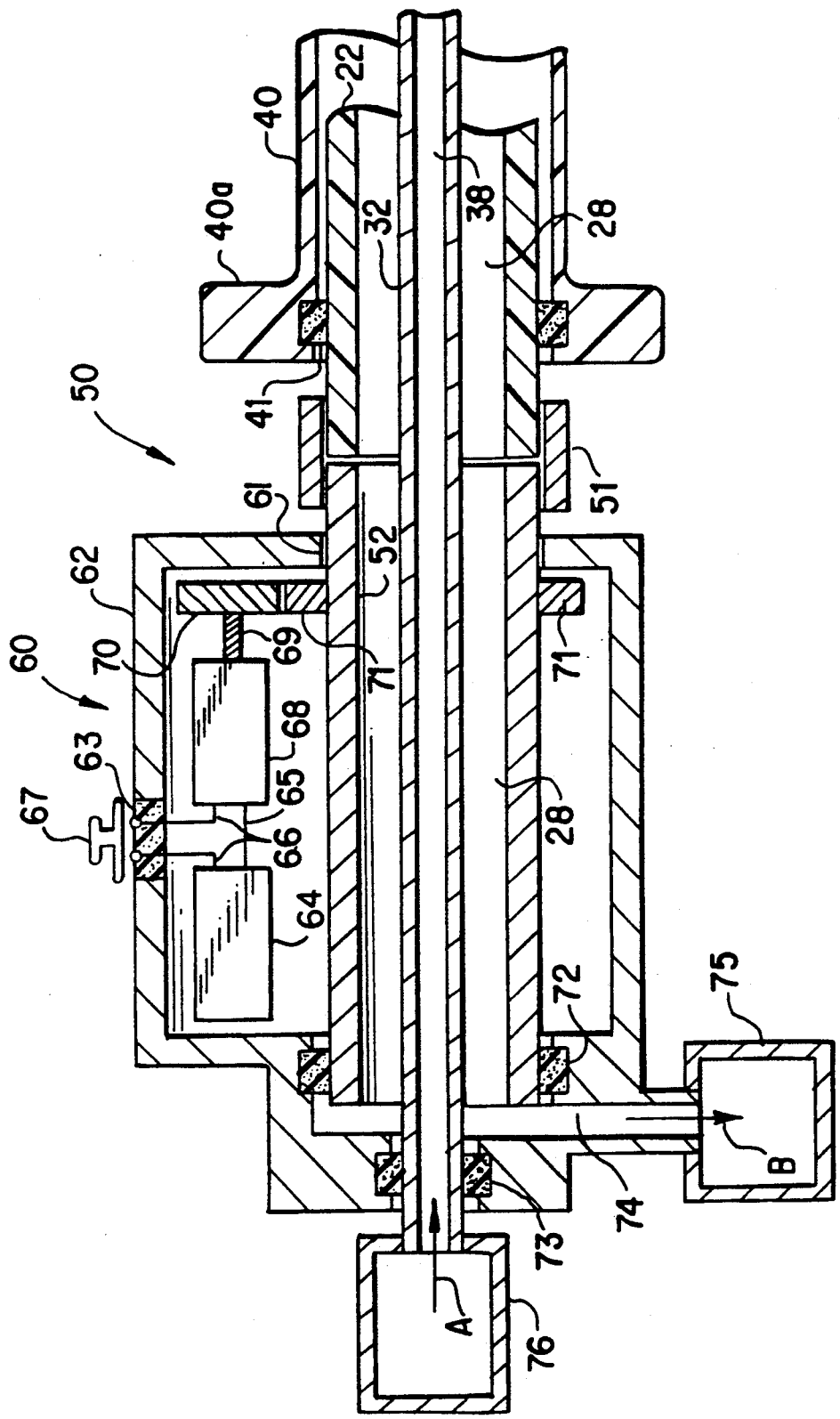
FIG. 8 is a longitudinal cross-sectional view of the proximal end of the ETAC system.

FIG. 1 is a longitudinal, cross-sectional view of the distal portion of the ETAC system 10 which consists of four major sub-systems; the ETAC 20, a balloon-on-a-guide-wire 30, a sheathing catheter 40, and a rotator unit 60 (FIG. 8). The ETAC 20 consists of a torquing catheter 22 whose proximal end extends outside the patient's body (see FIG. 8) and whose distal end 22a is attached to the proximal end of an elastomer web 26 and also to the proximal end of a plurality of metallic, spring-like spokes 24. FIG. 2 is a transverse cross section at 2—2 of FIG. 1 showing a lumen 38 inside the hollow guide wire cylinder 32 and passageway 28 within the torquing catheter 22 which at the distal end 22a lies within an elastomer web 26. FIG. 3, which is the transverse cross section at 3—3 of FIG. 1, shows a hole 24c through the spoke 24 which allows a button 26a of elastomeric material to help secure the distal end of the web 26 to the spoke 24. The web 26 is typically made from a plastic material such as silicone rubber, polyurethane or a comparable elastomer.

The portion of the spoke 24 located distally from the web 26 is free of webbing and is designed so as to both cut and/or grind (collectively termed "excise") the stenotic material that would be encounted by the distal end of the ETAC 20 as it is advanced while rotating through an arterial stenosis.

Figure 6:
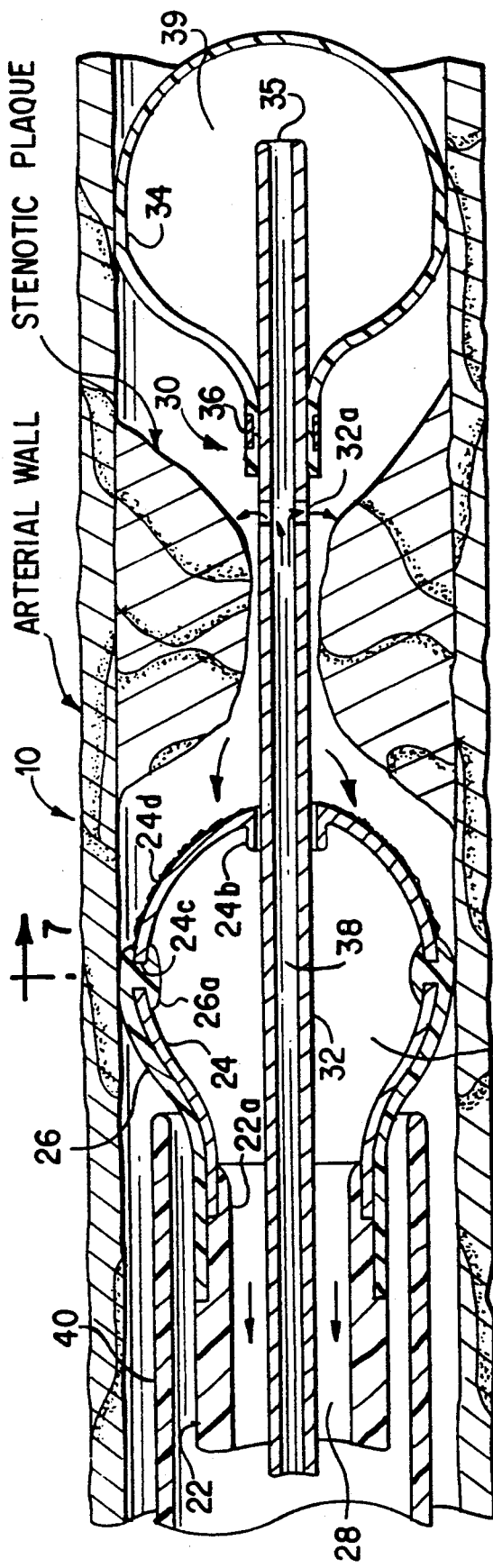
FIG. 6 is a longitudinal cross-sectional view within an artery of the ETAC system in its expanded state.

FIG. 1 shows the ETAC 20 in its compressed state. The spokes 24 are designed so that when the sheathing catheter 40 is pulled back to uncover the spokes 24, (as is shown in FIG. 6) the mechanical energy stored in the compressed spokes 24 will cause them to expand in a radially outward direction to a greater diameter as is also shown in FIG. 6. The spokes 24 are made from a metal such as spring steel or beryllium copper or another well known spring material. The spokes 24 are formed to natually extend to a diameter that is at least as great as the largest diameter of the web 26 when that web 26 is in its expanded state as shown in FIG. 6. Thus the mechanical spring energy of the spokes 24 causes them and the web 26 to both extend radially outward when the sheathing catheter 40 is pulled back sufficiently so as to completely uncover the spokes 24.

Figure 4:
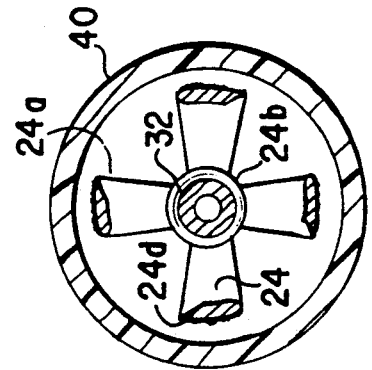
FIG. 4 is a transverse cross-sectional view of the ETAC system at a point where there is no plastic webbing over that portion of the spokes that cut and/or grind the plaque; specifically at 4—4 of FIG. 1.
Figure 5:
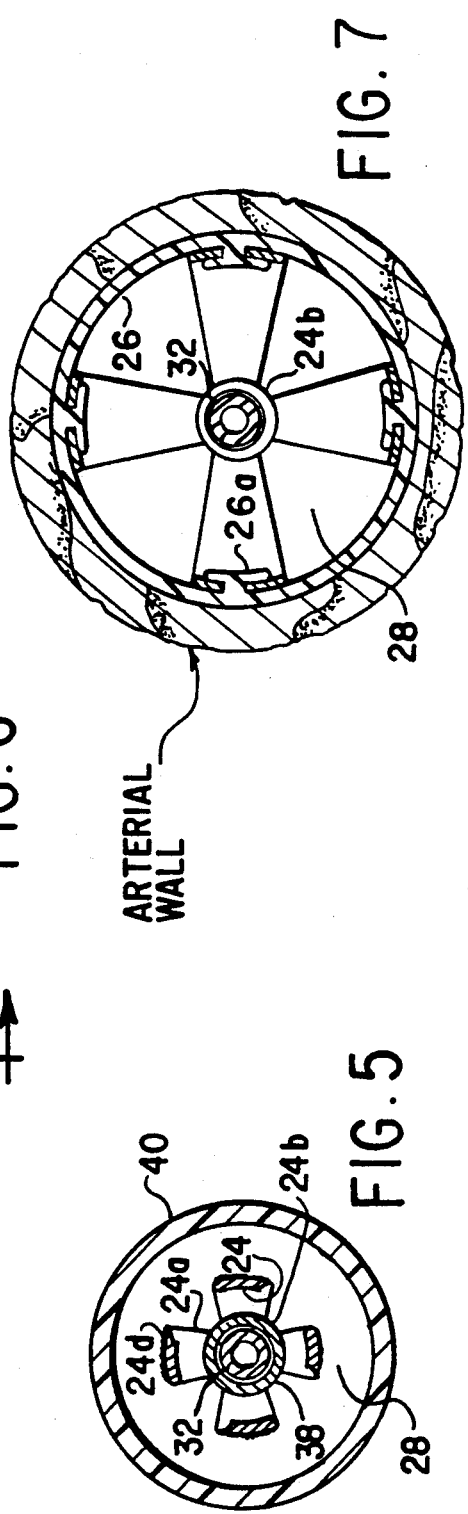
FIG. 5 is a transverse cross-sectional view of the ETAC system showing the short distal cylinder that slides over the hollow guide wire; specifically at 5—5 of FIG. 1.

The portion of the spokes 24 lying distally from the web 26 have a sharpened edge 24a as seen in FIG. 4 which is the transverse cross section at 4—4 of FIG. 1. The outer surface of the distal portion of the spokes 24 could have an abrasive surface 24d that is capable of grinding stenotic material as the ETAC 20 when expanded is advanced over the guide wire body 32 and into the stenotic plaque as shown in FIG. 6. The abrasive surface 24d of the spokes 24 could be obtained by a roughening treatment of the outer surface such as knurling, or by the application of an abrasive coating such as diamond or Carborundum particles. The most distal end of the spokes 24 attach to a cylinder 24b whose interior diameter is sized to move slideably along the guide wire body 32. This is illustrated in FIG. 5 which is the transverse cross section of the ETAC system 10 at position 5—5 of FIG. 1.

The annular passageway 28 between the outside surface of the guide wire cylinder 32 and the interior surface of the web 26 and catheter 22 (as also shown in FIGS. 2, 3, 5 and 7) allows fluid communication between the distal portion of the ETAC 20 and the proximal end of the catheter 22 that lies outside the patient's body. Fluid communication is necessary in order to inject contrast medium into the artery for angiography, or for injecting a flushing saline solution, or for therapeutic drugs, or, in the reverse direction, to suction out fluid and excised plaque from the atherectomized stenotic plaque as the ETAC 20 while rotating is advanced through the arterial stenosis.

The balloon-on-a-guide-wire 30 has a hollow guide wire cylinder 32 which extends outside the patient's body at its proximal end (see FIG. 8) and is attached near its distal end to an expandable balloon 34 which is held onto the guide wire cylinder 32 by a metallic ring 36. FIG. 1 shows the balloon 34 in its unfilled state and also shows fluid ports 32a in the cylinder 32 which ports 32a are located just proximal to the balloon 34. The cylinder 32 extends to the most distal end of the balloon 34 so that it shapes the unfilled balloon to be long and of small diameter so as to readily penetrate through a narrow stenosis. A fluid port 35 at the most distal end of the cylinder 32 allows the balloon to be in fluid communication with the proximal end of the cylinder 32 so as to readily inflate or deflate the balloon 34 as required for the atherectomy procedure. The guide wire cylinder 32 would typically be made from a very thin-walled spring metal or may be formed with a somewhat thicker wall from a plastic such as PVC, Teflon, Nylon or equivalent or from a helical metal spring wire encased in plastic. The elastomer balloon 34 might typically be formed from a silicone or latex rubber or an equivalent elastomer.

Figure 7:
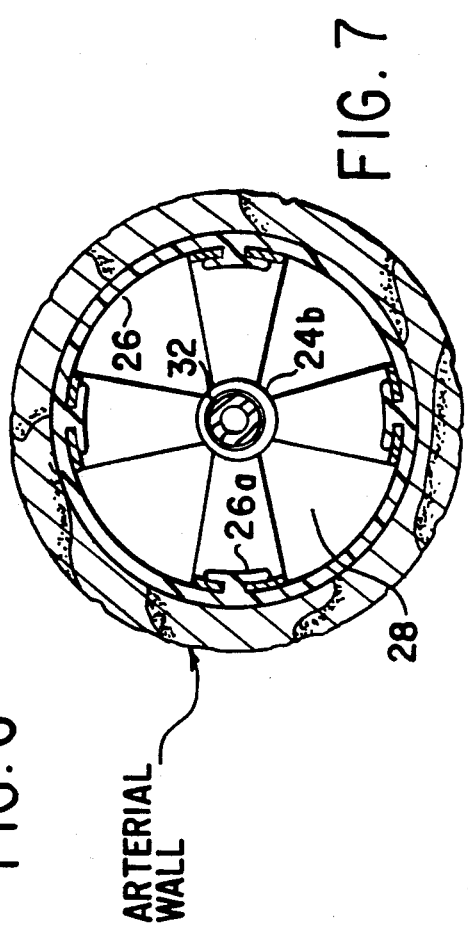
FIG. 7 is a transverse cross-sectional view of the distal portion of the ETAC system in its expanded state at its point of maximum diameter; specifically at 7—7 of FIG. 2.

FIG. 6 is a longitudinal, cross-sectional view of the distal end of the ETAC system 10 showing the ETAC 20 in its expanded state with the sheathing catheter 40 pulled back. As previously described, the mechanical energy stored in the spokes 24 causes them to expand until their radially outward travel is limited by the web 26 or the interior surface of the arterial wall. This is also illustrated in FIG. 7 which is the transverse cross section of the ETAC system 10 at position 7—7 of FIG. 6.

At approximately the same time as the sheathing catheter 40 is pulled back, the balloon 34 is expanded thus occluding the artery distal to the stenosis. The ports 32a in the guide wire cylinder 32 are sized so that a pressure between 0.01 and 1.0 atmospheres can be maintained in the balloon 34 so that it remains properly inflated while at the same time the balloon filling fluid (typically normal saline or contrast solution) flows through the lumen 38 and the ports 32a and then in a retrograde direction through the annular passageway 28 and back out of the patient through the proximal end of the catheter 22. The flow resistance of the ports 32a must be sufficient so that even when suction is applied at the proximal end of the catheter 22, sufficient fluid pressure is maintained in the interior chamber 39 of the balloon 34 to keep it inflated during the atherectomy procedure. Thus one or more ports (two are shown) with a diameter between 1 and 20 mils could be used to provide adequate flow while keeping the balloon 34 inflated. The arrows in FIG. 6 indicate the direction of fluid flow.

Another purpose of the non-rotating occluding balloon 34 is to prevent twisting of the artery as the spokes 24 are advanced through the stenotic plaque.

The proximal end 50 of the ETAC system 10 is shown in FIG. 8. The sheathing catheter 40 can be pulled back to release the expandable spokes 24 (of FIG. 6) by pushing the handle 40a in a retrograde direction (to the left in FIG. 6). A seal 41 prevents fluid or blood from leaking out between the sheathing catheter 40 and the torquing catheter 22. A pressure tight mechanical coupling 51, which could be a Luer lock fitting; joins the catheter 22 to the rotating cylinder 52.

The atherectomy procedure is accomplished by rotating the ETAC 20 using an appropriate rotator unit 60 that is attached at the proximal end of the torqueing catheter 22 as seen in FIG. 8. The rotator unit 60 consists of an outer casing 62 that has a bearing surface 61 at its distal end and a seal 72 near its proximal end and a second seal 73 at its proximal end. When a push button switch 67 mounted on the casing 62 is caused to close by finger pressure, the electrical wires 66 that are mounted in the insulator 63 are electrically connected thereby causing the battery 64 through wires 65 and 66 to be connected to the d-c electric motor 68 resulting in rotation of the motor shaft 69. This in turn causes rotation of the spur gear 70, which in turn causes rotation of the following spur gear 71, which in turn causes rotation of the cylinder 52 which, through the mechanical coupling 51 with the torquing catheter 22, causes the distal cutting/grinding (excising) end of the ETAC 20 to rotate the motor 68 could include an attached set of gears that could make the final rotational speed of the ETAC 20 lie between 500 and 100,000 RPM depending on whether cutting or grinding was the more promising method for stenotic plaque removal. Lower speeds would be used for softer plaques and higher speeds would be used for harder plaques. Rotators 60 having different set speeds could be selected depending on the type of plaque observed in a particular patient. It is also conceived that a variable speed d-c electric motor could be used in which a particular speed is set by the operator again depending on the hardness or other attributes of the stenotic plaque.

FIG. 8 also shows a fluid source 76 that is attached at the proximal end of the non-rotating guide wire cylinder 32. The fluid could be contrast media, flushing solution, saline solution, a medication to prevent arterial spasm or a blend of the above or any liquid that is useful for this procedure. The source of the fluid could be a hypodermic syringe, a bottle at some elevated height to provide pressure, or a pump or any other means to provide fluid at the desired working pressure. A suction means 75 would be connected to the passageway 74 which is in fluid communication with the passageway 28 interior to the cylinder 52. The suction means 75 could be a vacuum bottle or a vacuum pump or any other means capable of providing a negative pressure between −0.1 and −1.0 atmosphere. Both the fluid pressure source 76 and the suction means 75 would each have valves (not shown) that can be used to turn them on and off either separately or simultaneously. The typical use would be to turn both the fluid source 76 and the suction means 75 on and off together. The arrows A and B in FIG. 8 indicate the direction of fluid flow during the excising of the stenotic plaque. The direction of the fluid flow arrow A is reversed when it is desired to deflate the occlusive balloon 34 immediately prior to removing the ETAC system 10 from the patient's artery.

The operation of the ETAC system 10 would be as follows:

(1) A hollow needle puncture is made in the groin at the site of the femoral artery as is typically done for balloon angioplasty.

(2) The balloon-on-a-guide-wire 30 is advanced through the arterial system until the proximal end of the balloon 34 lies distal to the stenosis to be atherectomized as shown in FIG. 6.

(3) The ETAC 20, compressed within the sheathing catheter 40, is advanced over the guide wire cylinder 32 until the ETAC's distal end lies just proximal to the stenosis.

(4) The sheathing catheter 40 is pulled back thus allowing the spokes 24 of the ETAC 20 to expand.

(5) Contrast medium is injected at the proximal end of the ETAC 20 to verify the proper positioning of the ETAC system 10.

(6) Saline solution or contrast medium is injected through the lumen 38 of the guide wire cylinder 32 which inflates the balloon 34 and starts the retrograde flow of fluid through the passageway 28.

(7) While continuing to inject fluid into the lumen 38 of the guide wire cylinder 32, suction is applied at the proximal end of the catheter 22 while simultaneously rotating and advancing the spokes 24 through the stenosis.

(8) Once the entire stenosis has been atherectomized as seen in fluoroscopy, the rotational and forward motions of the ETAC 20 are both stopped and at that time or some short time afterward, the fluid flow into the lumen 38 and the application of suction to the passageway 28 are each discontinued.

(9) The sheathing catheter 40 is then advanced over the spokes 24 to compress them and the entire ETAC system 10 (with the balloon 34 deflated) is pulled out of the body.

There are many advantages of this system over the prior art some of which are as follows:

(1) The sheathing catheter can serve the classical function of a guiding catheter or sheath which function is well known in the art of angioplasty and atherectomy while also serving its unique sheathing and unsheathing functions and helping to prevent twisting of the artery during atherectomy.

(2) The distal end of the ETAC 20 can be expanded after insertion in the artery in order to provide an anterograde cutting atherectomy system which has a small diameter where it enters the body and throughout the arterial system except where it is actually cutting the plaque, and there it can excise stenotic tissue at a significantly larger diameter as compared to its diameter where it is percutaneously inserted through the groin.

(3) The combination of a cutting edge 24a and a grinding surface 24d of the spokes 24 allows both very hard or very soft plaque or anything in between to be atherectomized. It is also not necessary to know in advance the hardness of the stenotic plaque in order to have efficient atherectomy. However, the rotational speed might be adjusted to be slower for softer plaque and faster for harder plaque.

(4) The occlusive balloon prevents any particulate matter released during atherectomy from traveling downstream and also helps to prevent twisting of the artery during atherectomy and further prevents excessive blood loss during the procedure.

(5) The application of suction at the proximal end of the passageway 28 while simultaneously injecting or flushing fluid through the port 32a is an improved method for washing particulate matter cut or ground off the plaque from entering the bloodstream.

(6) Using the same fluid passageway for both occlusive balloon filling and for flushing eliminates the need for an extra lumen.

(7) Doing all of item 6 above with what is essentially a guide wire, eliminates the need for a separate guide wire.

Although a specific embodiment of the ETAC system 10 is described herein, these teachings suggest other alternative designs as well such as:

(1) Having two separate lumens in the guide wire cylinder 32; one to fill the balloon 34 and the other to inject fluid into the passageway 28;

(2) The balloon 34 could instead be an expandable mesh that allows small particulate matter to go through up to the size, for example, of white blood cells;

(3) A separate guiding catheter could be used instead of using the sheathing catheter 40 for that function;

(4) The spokes 24 could have either a cutting edge or a grinding surface but not necessarily both;

(5) The occlusive balloon 34 and other novel concepts described herein could also be used with the Expandable Pullback Atherectomy Catheter as described in the previously cited patent application, U.S. Ser. No. 153,912 which is included herein by reference.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A catheter system for atherectomy of arterial stenotic plaque from an artery comprising;
    a guide wire which can be passed through said arterial stenotic plaque;
    an atherectomy catheter having a distal end and a proximal end and having an interior passageway throughout the catheter's entire length configured to allow the guide wire to be moved slideably through the entire length of the passageway, the atherectomy catheter also having a plurality of expandable sharpened cutting blades located near the catheter's distal end which cutting blades are retained at a first and smaller diameter as the catheter is inserted into the artery;
    a sheathing catheter which encloses the cutting blades and which allows the sharpened cutting blades to expand outwardly to a second and larger diameter prior to the cutting of the stenotic plaque when the sheathing catheter is pulled backward in a proximal direction;
    a means attached to the atherectomy catheter's proximal end for simultaneously rotating and advancing the plurality of expandable cutting blades set at the second and larger diameter through the stenotic plaque while retaining the guide wire in a fixed position within the artery;
    a means for removing the cut plaque from the artery after the plaque has been cut off the arterial wall; and
    a means for urging the sheathing catheter to move forward in a distal direction relative to the cutting blades so as to return the plurality of cutting blades to said first and smaller diameter before removing the atherectomy catheter from the artery.

2. The catheter system of claim 1 wherein the plaque removing means further comprises a suction means whereby a suction can be applied at the proximal end of said atherectomy catheter to remove the cut arterial stenotic plaque as the expanded cutting blades are advanced through the arterial stenotic plaque.

3. The catheter system of claim 1 wherein the expandable cutting blades have a roughened outer surface for grinding the stenotic plaque from said artery.

4. The catheter system of claim 1 wherein said guide wire has an interior passageway throughout its entire length and also has an inflatable balloon at its distal end which is in fluid communication with the passageway, said inflatable balloon being adapted to be inflated from a source of pressurized fluid attached to an opening at the guide wire's proximal end, the opening being in fluid communication with the passageway, the inflatable balloon being adapted to block the artery downstream from said atherectomy catheter to prevent separated stenotic plaque from flowing downstream in said artery during the atherectomy procedure.

5. A catheter system for atherectomy of arterial stenotic plaque from an artery consisting of:
    a hollow cylindrical guide wire having a single interior passageway and having an inflatable balloon located near the guide wire's distal end, the balloon being in fluid communication with the passageway;
    a vent opening located in the wall of the hollow guide wire just proximal end of the balloon, the vent opening being in fluid communication with the passageway;
    a pressurized fluid source attached at the guide wire's proximal end, the pressurized fluid source being in fluid communication with the passageway;
    an atherectomy catheter having a plaque excising means located near its distal end and having a first interior lumen adapted to move slideably over the guide wire and having a second lumen connected to a suction source attached at the catheter's proximal end, the second lumen having a distal opening located near the atherectomy catheter's distal end;
    a means attached to the atherectomy catheter's proximal end for simultaneously rotating and advancing the atherectomy catheter over the guide wire so that the plaque excising means removes the stenotic plaque from the arterial wall while also pressurized fluid is injected simultaneously at the guide wire's proximal end for inflating the balloon and providing flushing fluid through the vent hole and also suction is simultaneously applied to the atherectomy catheter's second lumen for suctioning the flushing fluid and excised plaque out of the artery.

6. The catheter system of claim 5 wherein the atherectomy catheter's plaque excising means is expandable, the plaque excising means being inserted into the artery at a first and smaller diameter; and, a means for expanding the plaque excising means to a second and larger diameter for excising the plaque off the arterial wall.

7. A catheter system for atherectomy of arterial stenotic plaque from an artery consisting of:

a guide wire having two separate passageways, the first passageway being in fluid communication with an inflatable balloon located near the guide wire's distal end and the second passageway being in fluid communication with a vent opening located in the wall of the guide wire just proximal to the proximal end of the balloon;

a first pressurized fluid source attached at a first opening at the guide wire's proximal end, the first fluid source being in fluid communication with the first passageway;

a second pressurized fluid source attached at a second opening at the guide wire's proximal end, the second fluid source being in fluid communication with the second passageway;

an atherectomy catheter having a plaque excising means located near its distal end and having an interior lumen adapted to move slideably over the guide wire, said interior lumen being connected to a suction source attached at the atherectomy catheter's proximal end; and, a means attached to the atherectomy catheter's proximal end for simultaneously rotating and advancing the atherectomy catheter over the guide wire so that the plaque excising means removes the stenotic plaque from the arterial wall while also pressurized fluid is injected simultaneously at the guide wire's proximal end for inflating the balloon and providing flushing fluid through the vent hole and also suction is simultaneously applied to the atherectomy catheter's interior lumen for suctioning the flushing fluid and excised plaque out of the artery.

* * * * *